US007512576B1

United States Patent
Syeda-Mahmood et al.

(10) Patent No.: US 7,512,576 B1
(45) Date of Patent: Mar. 31, 2009

(54) AUTOMATICALLY GENERATED ONTOLOGY BY COMBINING STRUCTURED AND/OR SEMI-STRUCTURED KNOWLEDGE SOURCES

(75) Inventors: Tanveer F. Syeda-Mahmood, Cupertino, CA (US); Cartic Ramakrishnan, Fairborn, OH (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/014,876

(22) Filed: Jan. 16, 2008

(51) Int. Cl.
*G06F 17/00* (2006.01)
*G06N 5/00* (2006.01)

(52) U.S. Cl. .............................. 706/45; 706/46; 706/47

(58) Field of Classification Search .................. 706/45, 706/46, 47; 707/203
See application file for complete search history.

(56) References Cited

U.S. PATENT DOCUMENTS

| | | | |
|---|---|---|---|
| 6,263,335 B1 | 7/2001 | Paik et al. | |
| 6,487,545 B1 | 11/2002 | Wical | |
| 6,535,881 B1 * | 3/2003 | Baclawski | 707/10 |
| 6,675,159 B1 | 1/2004 | Lin et al. | |
| 7,099,885 B2 | 8/2006 | Hellman et al. | |
| 2006/0053098 A1 * | 3/2006 | Gardner et al. | 707/3 |
| 2006/0053099 A1 * | 3/2006 | Gardner et al. | 707/3 |
| 2006/0053135 A1 * | 3/2006 | Beaumont et al. | 707/101 |
| 2006/0053151 A1 * | 3/2006 | Gardner et al. | 707/102 |
| 2006/0053170 A1 * | 3/2006 | Hill et al. | 707/203 |
| 2006/0053171 A1 * | 3/2006 | Eldridge et al. | 707/203 |
| 2006/0053172 A1 * | 3/2006 | Gardner et al. | 707/203 |
| 2006/0053173 A1 * | 3/2006 | Gardner et al. | 707/203 |
| 2006/0053174 A1 * | 3/2006 | Gardner et al. | 707/203 |
| 2006/0053175 A1 * | 3/2006 | Gardner et al. | 707/203 |
| 2006/0074832 A1 * | 4/2006 | Gardner et al. | 706/45 |
| 2006/0074833 A1 * | 4/2006 | Gardner et al. | 706/45 |
| 2006/0074836 A1 * | 4/2006 | Gardner et al. | 706/60 |
| 2006/0074980 A1 | 4/2006 | Sarkar | |
| 2006/0179074 A1 | 8/2006 | Martin et al. | |
| 2007/0005621 A1 * | 1/2007 | Lesh et al. | 707/101 |
| 2007/0038594 A1 * | 2/2007 | Goodwin et al. | 707/2 |
| 2007/0162409 A1 | 7/2007 | Godden et al. | |
| 2007/0162465 A1 | 7/2007 | Cope | |
| 2007/0198449 A1 * | 8/2007 | Fokoue-Nkoutche et al. | 706/47 |
| 2007/0198578 A1 | 8/2007 | Lundberg et al. | |

OTHER PUBLICATIONS

Jianping Fan et al., Integrating Concept Ontology and Multitask Learning to Achieve More Effective Classifier Training for Multi-level Image Annotation, Mar. 2008, IEEE, 1057-7149, 407-426.*

* cited by examiner

*Primary Examiner*—Joseph P Hirl
(74) *Attorney, Agent, or Firm*—Cantor Colburn LLP; Van Nguy

(57) ABSTRACT

Exemplary embodiments of the present invention relate to a solution for the extraction of information from structured and semi-structured knowledge sources. Further, ontological relationships are inferred between the extracted information by parsing the layout structure of the structured and semi-structured knowledge sources. The inferred ontological relationships are verified in relation to existing ontological sources.

2 Claims, 2 Drawing Sheets

Congestive heart failure

Congestive heart failure (CHF), also called congestive cardiac failure (CCF) or just heart failure, is a condition that can result from any structural or functional cardiac disorder that impairs the ability of the heart to fill with or pump a sufficient amount of blood throughout the body. it is not to be confused with "cessation of heartbeat", which is known as asystole, or with cardiac arrest, which is the cessation of normal cardiac function in the face of heart disease. Because not all patients have volume overload at the time of initial or subsequent evaluation, the term "heart failure" is preferred over the older term "congestive heart failure". Congestive heart failure is often undiagnosed due to a lack of a universally agreed definition and difficulties in diag particularly when the condition is considered "mild".

| Congestive heart failure | |
|---|---|
| ICD-10 | 150-0 |
| ICD-9 | 428 |

Content [hide]

1 Causes
2 Classification
3 Signs and Symptons
4 Treatment
    4.1 Non-pharmacological measures
    4.2 Pharmacological management
        4.2.1 Angiotensin-modulating agents
        4.2.2 Diuretics
        4.2.3 Beta blockers
        4.2.4 Positive inotropes
        4.2.5 Alternative vasodilators
    4.3 Devices and surgery
5 See also
6 External links
7 References
8 See also navigation
- Main Page
- Community Portal
- Featured articles
- Current events
- Recent changes
- Random article
- Help
- Contact Wildpedia
- Donations search
[Go] [Search]

toolbox
- What links here
- Related changes
- Upload file
- Special pages
- Printable version
- Permanent Link
- Cte this article

In other languages
- Deutsch
- Español

FIG. 1

AUTOMATICALLY GENERATED ONTOLOGY BY COMBINING STRUCTURED AND/OR SEMI-STRUCTURED KNOWLEDGE SOURCES

BACKGROUND OF THE INVENTION

1. Field of the Invention

This invention relates to the creation and organization of ontology and particularly to the automatic creation of ontology from structured and semi-structured knowledge sources.

2. Description of Background

Ontologies are data models for the modeling of the concepts and the relationship between a set of concepts. Ontologies are utilized to illustrate the interaction between the set of concepts and corresponding relationships within a specific domain of interest. Thus, the concepts and the relationships between the concepts can be represented in readable-text, wherein descriptions are provided to describe the concepts within a specific domain and the relationship axioms that constrain the interpretation of the domain specific concepts.

SUMMARY OF THE INVENTION

The shortcomings of the prior art are overcome and additional advantages are provided through the provision of a method for generating ontology based upon data obtained from structured and semi-structured knowledge sources. The method comprises determining a primary subject on which an ontology is to be based, determining concepts of interest related to the subject, and relationships that are to be associated with concepts, determining at least one information source, analyzing at least one information source in order to extract topic concepts that match the primary subject in addition to content that is associated with the topic concepts, and identifying within the content that is associated with the subject, relationship references that are associated with the topic concepts, wherein the relationship references respectively correspond to the determined ontology relationship references.

The method further comprises extracting predetermined concept descriptors from the content that is associated with the relationship references, associating the concept descriptor with the ontology relationship reference that corresponds to the relationship reference, analyzing at least one information source in order to further identify concept descriptors that match the identified concept descriptors and content that is associated with the concept descriptors, and identifying within the content that is associated with a respective concept descriptor relationship references that are associated with the concept descriptor, wherein the relationship references respectively correspond to the determined ontology relationships.

The method yet further comprises extracting concept descriptors from the content that is associated with the relationship references, analyzing the ontology relationship references that are associated with a parent concept descriptor and a child concept descriptor, validating the relationship between the parent concept descriptor and the child concept descriptor, wherein the instance that the relationship between the parent concept descriptor and the child concept descriptor is valid then the child concept descriptor is annotated as a direct ontology relationship reference of its parent concept descriptor, and generating a primary topic concept specific ontology.

Computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 is a screenshot of a webpage whose information can be accessed via exemplary embodiments of the present invention.

Figure 2:
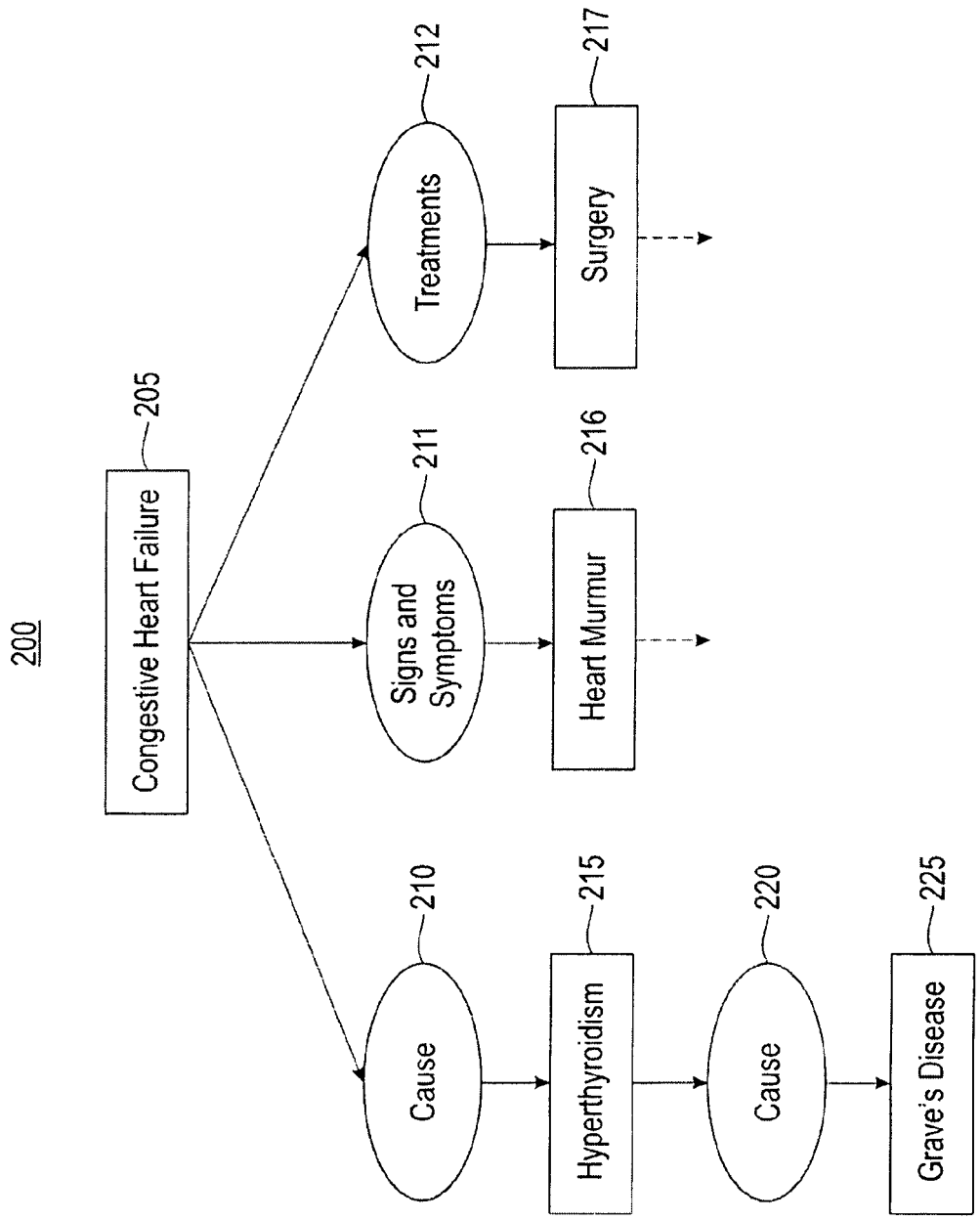
FIG. 2 illustrates one example of a section of the ontology that was created in accordance with exemplary embodiments of the present invention.

The detailed description explains the preferred embodiments of the invention, together with advantages and features, by way of example with reference to the drawings.

DETAILED DESCRIPTION OF THE INVENTION

One or more exemplary embodiments of the invention are described below in detail. The disclosed embodiments are intended to be illustrative only since numerous modifications and variations therein will be apparent to those of ordinary skill in the art.

Aspects of the exemplary embodiment of the present invention can be implemented within a conventional computing system environment comprising hardware and software elements. Specifically, the methodologies of the present invention can be implemented to program a conventional computer system in order to accomplish the prescribed tasks of the present invention as described below.

Exemplary embodiments of the present invention relate to a solution for the extraction of information from structured (e.g., HTML webpage, etc.) and semi-structured knowledge source information (e.g., annotated XML, information). Further, ontological relationships are inferred between the extracted information by parsing the layout structure of the structured and semi-structured knowledge sources in order to identify specific information. The inferred ontological relationships are verified in relation to existing ontological sources as available.

Within exemplary embodiments of the present invention a set of subject-matter specific relationships is established as a logical foundation for the ontological subject matter domain. The subject-matter specific relationships can be derived partially from a pre-existing information source (e.g., the Unified Medical Language System (UMLS) semantic network) and partially from the knowledge that need to be modeled for an identified subject. For example, an ontology on the subject of cardiovascular diseases will use cardiovascular diseases as topic concepts while the relationships may correspond to disease-specific relationships such as symptoms, causes, treatments, etc. Once the subject-matter specific relationships have been established a structured or semi-structured knowledge source is parsed in order to identify topic headings and content text that is associated with respective topic headings within the structured or semi-structured knowledge source. The topic headings that are identified within the structured or semi-structured knowledge source correspond to the predetermined subject-matter specific relationship.

The textual content is then analyzed to identify references to concepts—wherein concept reference descriptors can be obtained identified by a system user or extracted from a pre-existing information source. Within exemplary embodiments of the present invention the relationship between concepts is semantically derived partially from document layout (e.g., a section heading of "Causes" followed by a bulleted list of concepts can be used to infer a causal relationship between the enumerated list of concepts and the parent concept highlighted in the document). For each concept reference descriptor that is identified, an analysis is performed of the textual content, information to identify references to concept descriptors that exist within the textual content information. Further, any textual content information that is associated with a child content descriptor of an identified reference to a content descriptor is analyzed in order to identify any additional content descriptor references.

A relationship is inferred between two differing concepts based upon the topic heading under which the concepts were identified (e.g., if a topic/relationship is identified as being a "Cause" of a certain outcome, then identified concepts and child concepts and the relationship between the parent and child concept can be inferred to be "Causes" also). The relationship between a concept and a topic/relationship, and a concept and a child concept can be validated where possible within exemplary embodiments of the present invention by performing a comparison analysis of the identified topic/relationships, concepts, child concepts, and the relationships between the entities and a pre-existing information source (e.g., the UMLS semantic network as mentioned above). Once a relationship is identified between a parent and child concept, then a link within an ontology is populated with an annotation identifying the relationship between the two concepts. The process is repeated until for all identified concepts until no more new relationships can be extracted. The resultant ontology is displayed to a user for verification via a display device or can be output as a hardcopy or delivered to an additional software application for further processing.

An exemplary embodiment of the present invention will be described wherein an ontology within the medical domain will be generated for the subject-matter pertaining to cardiovascular diseases. In particular, such an ontology can be of use as clinical decision support as a diagnosis validation tool. The ontology can act as a knowledge source for the automatic validation of information that is provided in a patient's clinical record. Further, the ontology can be used as an additional reference source by physicians, thus allowing for physicians to make more informed diagnoses.

Currently, the UMLS is the largest source of medical knowledge; however, no specific ontologies for cardiovascular disease diagnosis exist. The UMLS embodies knowledge from multiple sources including Medical Subject Headings (MeSH), Systematized Nomenclature of Medicine (SNOMED), Logical Identifiers Names and Codes (LOINC), as well as relationships between differing concepts using a semantic network. These ontologies capture generic relations between diseases, anatomical regions, etc. Thus, due to the unstructured nature of the knowledge represented within their descriptors, it is difficult to make inferences and apply reasoning engines to such manually assembled knowledge sources.

Therefore, the above-mentioned ontologies cannot be directly used to answer questions such as: What are the causes of cardiomyopathy (thus providing a listing of causes which could be other diseases); Tell me about cardiomyopathy (thus providing a descriptive text as an answer). Finding answers to diagnosis-specific questions such as these would involve not only inference on the existing medical knowledge ontologies such as MeSH or SNOMED, but also correlating the unstructured text information that can identified within descriptions of diseases—with the corresponding relationships captured within medical ontologies.

A cardiovascular ontology can be automatically assembled within exemplary embodiments of the present invention by predefining disease diagnosis-specific relationships and applying the disease diagnosis-specific relationships to extracted disease-specific information from structured or semi-structured textual knowledge sources. In particular, as shown in FIG. 1 an annotated XML source webpage (e.g., a webpage from Wikipedia the web-based free content encyclopedia content) is accessed in order to extract text descriptions and relationships. Additionally, ontologies extracted from UMLS can be utilized to recognize the disease labels and to verify the validity of relationships when available.

FIG. 1 shows a sample webpage 100 that illustrates the semi-structuring of knowledge within an XML, construct. While the visual layout of the webpage is meant for human consumption, within exemplary embodiments, the information contained within the webpage can be captured and represented within a cardiovascular ontology in order to allow deduction of such knowledge through inference. A segment of a generated cardiovascular ontology 200 in reference to congestive heart failure is shown in FIG. 2. As shown in FIG. 2, the inference that Grave's disease is a cause of congestive heart failure is made possible through our ontology even though this conclusion is not directly referred to either in the webpage or in UMLS.

The ontology 200 in regard to congestive heart failure is initiated by the identification of the disease-specific relationships that are to be captured in the ontology 200. A listing of relationships is described as follows:

Describe/References—What is X?/All references of X
Diagnosis/Diagnosis uses—How is X diagnosed?/What is X used to diagnose?
Causes/Caused by—What are the causes of X?/What are caused by X?
Pathology/Pathology involvement—What is the pathology of X?/Which disease pathology is X involved in ?
Etiology/Etiology involvement—What is the etiology of X?/What is X an etiology of?
Used for/Uses—What is X used for?/What does X use?
Contra-indications/Contra-indications involvement—What are the contra-indications of X?/What is X a contra-indication of?
Complications/Complications involvement—What are the complications of X?/What is X a complication of?
Severity Levels/Severity relation—What are the severity levels of X?/Is X a severity level of another disease?
Genetic Causes/Genetic effects—What are the genetic causes of X?/What genetic effects are due to X'?
Physiology/Physiological effects—What is the physiology of X?/What physiological effects are due to X?
History/Affects history—What is the history of X?/What history effects are due to X?
About/About—Other Descriptions involving X/Tell me about X Upon the establishment of the disease-specific relationships a structured (e.g., a HTML document) or semi-structured knowledge source is parsed in order to identify topic headings/relationships that exist within the knowledge source and content that is contained under the topic heading. In the case of a web page such as Wikipedia that is annotated in XML, the topic headings are the main subject headings and subheadings, and the content under the topic is considered free text. For a structured document such as an HTML webpage, the information content of the webpage is tagged according to the HTML programming protocol, wherein information can be extracted from a webpage according to the corresponding tag that is associated with differing content segments that are contained within the webpage.

Next, information that has been obtained from the UMLS ontology is utilized to prune the free text content that is associated with a heading or sub-heading in order to isolate concept words that correspond to disease-related descriptors that as specified by MeSH. For each such concept word, a relation is inferred between two concepts utilizing the topic heading that the concepts have been identified as being associated. For example, a topic heading of "Causes" and a listing of "Causes" can be used to infer the relationship between two concepts to be either "causes" or "caused by," 210, 220 as shown in FIG. 2.

The relationship between two concepts 215, 225 is validated by comparing the identified relationships against a verified information source wherever available, such as the UMLS semantic network comprising captured relationships between MeSH concepts. In the instance that a relationship is validated, the relationship is added as a link 210-212, 220 between the two concept nodes 215 and 225 in the ontology 200. The concept validation operation is repeated until all of the identified concepts have been analyzed. Thereafter, the ontology that is based upon the original primary topic is completely generated. Thus, by a cursory review of the ontology segment presented in FIG. 2 we are able to distinguish the relationship of congestive heart failure 205/hyperthyroidism 215 as a causal 210 relationship from another of congestive heart failure 205/surgery 217 which is a treatment 212 relationship. It must be noted that the validation step is optional. Within exemplary embodiments of the present invention ontology links will be added between concept nodes even in the event that verification with an existing knowledge source cannot be performed.

The capabilities of the present invention can be implemented in software, firmware, hardware or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A method for generating computer implemented ontology based upon data obtained from structured and semi-structured knowledge sources, the method comprising:

determining a primary topic concept on which an ontology is to be based;

determining, from a derivation of the Unified Medical Language System (UMLS) semantic network, ontology relationship references that are to be associated with all concepts that are comprised within the ontology;

retrieving at least one information source;

analyzing the at least one information source in order to identify a topic concept that matches the primary topic concept in addition to content that is associated with the topic concept;

identifying within the content that is associated with the topic concept, relationship references that are associated with the topic concept, wherein the relationship references respectively correspond to the determined ontology relationship references;

extracting predetermined concept descriptors from the content that is associated with the relationship references;

associating the concept descriptor with the ontology relationship reference that corresponds to the relationship reference;

analyzing the at least one information source in order to further identify concept descriptors that match the extracted concept descriptors and content that is associated with the concept descriptors;

identifying within the content that is associated with a respective concept descriptor relationship references that are associated with the concept descriptor, wherein the relationship references respectively correspond to the determined ontology relationships;

extracting concept descriptors from the content that is associated with the relationship references;

analyzing the ontology relationship references that are associated with a parent concept descriptor and a child concept descriptor;

validating the relationship between the parent concept descriptor and the child concept descriptor by capturing a corresponding relationship from the UMLS semantic network and comparing the relationship between the parent concept descriptor and the child concept descriptor to the relationship captured from the UMLS semantic network, wherein the instance that the relationship between the parent concept descriptor and the child concept descriptor is validated then the child concept descriptor is annotated as a direct ontology relationship reference of its parent concept descriptor; and generating a primary topic concept specific ontology.

2. The method of claim 1, wherein the information source can comprise one or a combination of a structured information source and a semi-structured information source.

* * * * *